(12) United States Patent
Lovejoy et al.

(10) Patent No.: US 6,453,186 B1
(45) Date of Patent: Sep. 17, 2002

(54) ELECTROCARDIOGRAM ELECTRODE PATCH

(75) Inventors: David Anthony Lovejoy, Thiensville; George Alexander Byers, Milwaukee; Patricia J. Mikula, Thiensville, all of WI (US)

(73) Assignee: GE Medical Systems Information Technologies, Inc., Waukesha, WI (US)

(*) Notice: Subject to any disclaimer, the term of this patent is extended or adjusted under 35 U.S.C. 154(b) by 0 days.

(21) Appl. No.: 09/681,470

(22) Filed: Apr. 13, 2001

(51) Int. Cl.[7] ............................................. A61B 5/0408
(52) U.S. Cl. ..................... 600/386; 600/391; 600/392; 600/393
(58) Field of Search ........................ 600/372, 386–393

(56) References Cited

U.S. PATENT DOCUMENTS

| | | | | |
|---|---|---|---|---|
| 3,409,007 A | * | 11/1968 | Fuller .......................... | 600/393 |
| 3,534,727 A | * | 10/1970 | Roman ......................... | 600/389 |
| 3,888,240 A | * | 6/1975 | Reinhold et al. ............ | 600/390 |
| 4,353,372 A | * | 10/1982 | Ayer ........................... | 600/393 |
| 4,391,279 A | * | 7/1983 | Stein ........................... | 600/390 |
| 4,583,549 A | | 4/1986 | Manoli | |
| 4,763,660 A | * | 8/1988 | Kroll et al. .................. | 600/391 |
| 4,957,109 A | * | 9/1990 | Groeger et al. ............. | 600/393 |
| 5,184,620 A | | 2/1993 | Cudahy et al. | |
| 5,341,806 A | * | 8/1994 | Gadsby et al. .............. | 600/391 |
| 5,782,238 A | | 7/1998 | Beitler | |
| 5,788,633 A | | 8/1998 | Mahoney | |
| 5,868,671 A | | 2/1999 | Mahoney | |
| 5,916,159 A | | 6/1999 | Kelly et al. | |
| 5,951,598 A | | 9/1999 | Bishay et al. | |
| 6,055,448 A | * | 4/2000 | Anderson et al. ........... | 600/393 |
| 6,115,623 A | * | 9/2000 | McFee ........................ | 600/393 |

* cited by examiner

Primary Examiner—Lee Cohen
(74) Attorney, Agent, or Firm—Michael Best & Friedrich LLP (57) ABSTRACT

An electrocardiogram (ECG) electrode patch for attachment to a neonatal or infant patient. The ECG electrode patch includes a plurality of at least three electrodes coupled to a substrate. The plurality of at least three electrodes includes at least one electrode capable of measuring the electrical activity of the right side of the patient's heart. A plurality of electrical conductors are coupled to the plurality of electrodes and to the substrate.

89 Claims, 5 Drawing Sheets

ELECTROCARDIOGRAM ELECTRODE PATCH

RELATED APPLICATIONS

Priority is claimed under 35 U.S.C. §120 to U.S. patent application Ser. No. 09/583,405.

BACKGROUND OF THE INVENTION

The invention relates to an electrocardiogram (ECG) electrode patch and more particularly to an ECG electrode patch for attachment to a neonatal or infant patient.

ECG devices are medical devices that measure and record electrical potentials generated by a patient's heart. The ECG devices convert the electrical potentials into electrical signals or ECG data. The ECG data is displayed in the form of ECG waveforms on a display monitor or on a continuous stream of paper, called an ECG tracing. Generally, the ECG data is also stored electronically in a hospital storage facility.

For a standard twelve-lead ECG, ten electrodes are attached to the surface of the patient's body, with each electrode corresponding to a particular area of the patient's heart. Six of the ten electrodes (V1, V2, V3, V4, V5, and V6) are positioned on the left side of the patient's chest around the heart in order to detect the electrical activity of the left side of the patient's heart. Four of the ten electrodes are positioned on or near the patient's limbs. Specifically, the four limb electrodes are positioned on the right arm (RA), the left arm (LA), the right leg (RL), and the left leg (LL).

To detect the electrical activity of portions of the patient's heart other than the left side of the patient's heart, additional electrodes may be attached to the patient. Three electrodes (V4R, V5R, and V6R), referred to collectively as the right-sided chest leads, may be positioned on the patient's chest to measure the electrical activity of the right side of the patient's heart. Placement of the V4R, V5R, and V6R electrodes on the right side of the patient's chest mirrors the placement of the V4, V5, and V6 electrodes on the left side of the patient's chest.

The three right-sided chest electrodes are often used for neonatal and infant ECG diagnostic and monitoring procedures. The hearts of neonatal and infant patients are anatomically shifted more to the right of the body than the hearts of adult patients. Due to this difference in the anatomical location of the heart, it is necessary to monitor neonatal and infant patient's hearts with right-sided chest electrodes.

A primary concern when preparing a patient for an ECG procedure is the accurate placement of the electrodes. It is critically important that the electrodes be positioned at the positions associated with a standard twelve-lead ECG to ensure that the acquired signals yield universally acceptable diagnostic data. If the electrodes are not positioned properly or if they do not properly contact the patient's skin, the recorded data may be invalid.

Conventional electrodes are positioned individually on the patient with each electrode being coupled to a separate leadwire. For a standard twelve-lead ECG, ten conventional electrodes and ten leadwires are coupled to the patient. When the three right-sided chest leads are also attached to the patient, thirteen conventional electrodes and thirteen leadwires must be coupled to the patient.

Acquiring a multi-lead ECG for a neonatal or infant patient with conventional electrodes has several limitations. Accurately positioning and attaching as many as thirteen conventional electrodes to a neonatal or infant patient can be difficult and time consuming even for a skilled clinician. Conventional electrodes are physically to large to fit on the chest of neonatal and infant patients and do not adhere well to the skin of neonatal and infant patients. Moreover, clipping on as many as thirteen leadwires to the conventional electrodes is difficult because of the close proximity of each of the electrodes. During the positioning and attachment process, the leadwires also have a tendency to become tangled with one another.

Even if each of the electrodes are accurately attached to the patient initially, leadwires often become tangled and electrodes often detach from the patient's chest when the patient moves. These problems are magnified in the case of neonatal and infant patients whose movements cannot be controlled as easily as the movements of adult patients. Since conventional electrodes do not adhere well to the skin of neonatal and infant patients, the electrodes are even more likely to detach from the patient.

Even if the electrodes remain in place and the leadwires remain untangled while a first set of ECG data is acquired, it is difficult to repeat the exact placement of the electrodes in order to acquire subsequent sets of ECG data from the same patient. Clinicians often acquire subsequent sets of ECG data in order to periodically monitor the patient's recovery progress or to periodically monitor the patient's general cardiac health. The electrode placement for the subsequent sets of ECG data must be the same as the first set of ECG data in order to accurately compare the sets of ECG data.

Due to the difficulties in positioning and attaching conventional electrodes and leadwires to neonatal and infant patients to acquire a multi-lead ECG, multi-lead ECGs are acquired from neonatal and infant patients much less often than multi-lead ECGs are acquired from adult patients.

SUMMARY OF INVENTION

In light of the difficulties and limitations described above, a need exists for the easy, accurate, and consistent attachment of a plurality of electrodes to a neonatal or infant patient in order to acquire a multi-lead ECG.

Accordingly, the invention provides an ECG electrode patch for the easy, accurate, and consistent attachment of a plurality of electrodes to a neonatal or infant patient in order to acquire a multi-lead ECG.

The ECG electrode patch for attachment to a neonatal or infant patient's chest includes a substrate and a plurality of at least three electrodes coupled to the substrate. The plurality of electrodes includes at least one electrode capable of measuring the electrical activity of the right side of the patient's heart. The plurality of electrodes may include up to six left-sided chest electrodes, up to three right-sided chest electrodes, and up to four limb electrodes. A plurality of electrical conductors are coupled to the plurality of electrodes and to the substrate.

The ECG electrode patch may also include a plurality of layers including a flexible backing layer, a skin adhesive layer, a plurality of conductive gel layers, and a releasable liner layer. The ECG electrode patch may be coupled to an ECG machine with a single conductor.

The invention includes a method of acquiring a neonatal or infant patient's ECG including the acts of providing an ECG electrode patch, attaching the electrode patch to the patient's chest, and acquiring ECG data. The ECG electrode patch includes a plurality of electrodes, including at least one electrode capable of measuring the electrical activity of the right side of the patient's heart.

It is an advantage of the invention to reduce the labor and time associated with instrumenting a patient for an ECG procedure.

It is another advantage of the invention to ensure the repeatable and consistent placement of electrodes.

It is still another advantage of the invention to minimize the total material cost of a multi-lead ECG procedure.

It is still another advantage of the invention to eliminate the need for individual leadwires.

It is still another advantage of the invention to provide a low-profile detachable cabling system between the plurality of electrodes and the ECG machine.

It is still another advantage of the invention to improve the reliability and integrity of the acquired ECG data.

It is still another advantage of the invention to improve the procedure for acquiring multi-lead ECGs from neonatal and infant patients.

Various other features and advantages of the invention are set forth in the following drawings, detailed description, and claims.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 1:
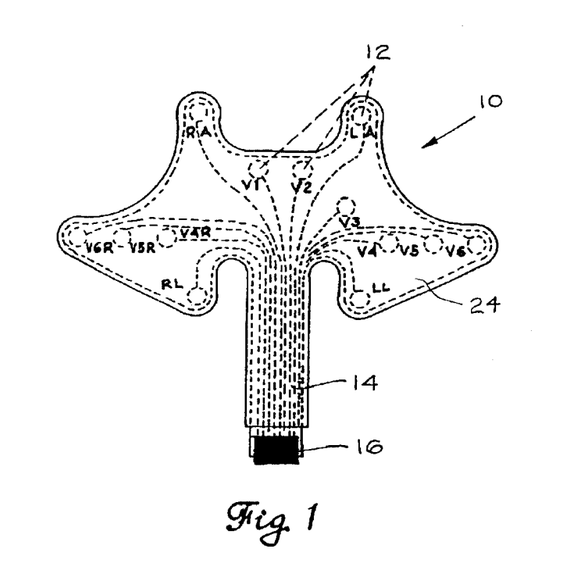
FIG. 1 is a front view of an ECG electrode patch.
Figure 2:
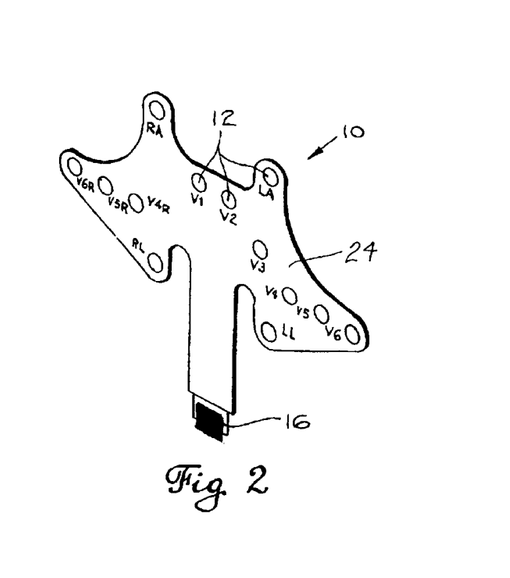
FIG. 2 is a perspective view of the ECG electrode patch of FIG. 1.

FIGS. 1 and 2 illustrate an ECG electrode patch 10 embodying the invention. The ECC electrode patch 10 includes a plurality of electrodes 12 coupled to a substrate 24, a plurality of electrical conductors 14 coupled to the plurality of electrodes 12 and to the substrate 24, and a common connector 16 coupled to the plurality of electrical conductors 14.

The plurality of electrodes 12 includes thirteen electrodes for acquiring a standard ten-electrode, twelve-lead ECG and three additional leads of ECG data. The plurality of electrodes 12 are positioned within the ECG electrode patch 10 so that when the ECG electrode patch 10 is accurately aligned and attached to the patient, the plurality of electrodes 12 acquire a standard twelve-lead ECG and three additional leads of ECG data.

In order for the electrodes to be accurately aligned and attached to the patient, the ECG electrode patch 10 must be designed according to the anatomy of the intended patient population. Preferably, the ECG electrode patch 10 is designed according to the anatomy of neonatal and infant patients. Generally, the ECG electrode patch 10 is designed for neonatal patients that weigh less than 3 kilograms and infant patients that weigh between 3 kilograms and 20 kilograms. Most preferably, one ECG electrode patch 10 is designed for the neonatal patient population and a separate ECG electrode patch 10 is designed for the infant patient population.

The plurality of electrodes 12 includes ten electrodes corresponding to the electrodes of a standard twelve-lead ECG. The plurality of electrodes 12 includes six left-sided chest electrodes, namely V1, V2, V3, V4, V5, and V6. The left-sided chest electrodes sense electrical potentials generated by the left side of the patient's heart. The left-sided chest electrodes are positioned within the ECG electrode patch so that when the patch is accurately attached to the patient, the electrodes are located in the electrode positions for a standard twelve-lead ECG. Specifically, the V1 electrode is positioned approximately at the fourth right intercostal space at the right border of the patient's sternum, the V2 electrode is positioned approximately at the fourth left intercostal space at the left border of the patient's sternum, the V3 electrode is positioned approximately midway between locations V2 and V4, the V4 electrode is positioned approximately at the mid-clavicular line in the fifth left intercostal space, the V5 electrode is positioned approximately at the anterior axillary line on the same horizontal level as V4, and V6 is positioned approximately at the mid-axillary line on the same horizontal level as V4 and V5.

The plurality of electrodes 12 also includes four limb electrodes, namely RA, LA, RL, and LL. Generally, for a standard twelve-lead ECG, one electrode is attached to each of the patient's right arm (RA), left arm (LA), right leg (RL), and left leg (LL). However, rather than placing the limb electrodes actually on the patient's limbs, an accurate ECG can be acquired by placing the limb electrodes on the patient's chest, as in methods such as Mason-Likar electrode placement. For example, in Mason-Likar electrode placement, the RA and LA electrodes are placed on the patient's chest just below the right and left clavicle, respectively. Similarly, in Mason-Likar electrode placement, the RL and LL electrodes are placed on the right and left sides, respectively, of the lower edge of the rib cage.

In the case of a neonatal or infant patient, the physical size of the patient's chest is much smaller than that of an adult patient. Since the physical size of the neonatal or infant's chest is smaller than that of an adult patient, the neonatal or infant patient's clavicles and rib cage are in closer proximity to the patient's heart than the clavicles and rib cage of an adult patient. As a result, for a neonatal or infant patient, the limb electrodes can be placed in close proximity to the chest electrodes. Thus, for a neonatal or infant patient, the limb electrodes can be placed along with the chest electrodes in a single ECG electrode patch 10. When the ECG electrode patch 10 is accurately attached to the neonatal or infant patient's chest, the limb electrodes are positioned within the ECG electrode patch 10 so that the RA and LA electrodes are in close proximity to the neonatal or infant patient's right and left clavicles and the RL and LL electrode are in close proximity to the lower edge of the patient's rib cage. Thus, an accurate ECG can be acquired from the neonatal or infant patient with a single ECG electrode patch 10, even though the limb electrodes are not attached to the neonatal or infant patient's actual limbs.

In addition to the ten electrodes necessary for a standard twelve-lead ECG, the plurality of electrodes 12 of the ECG electrode patch 10 also includes three right-sided chest electrodes, namely V4R, V5R, and V6R. The right-sided chest electrodes sense electrical potentials generated by the right side of the patient's heart. Placement of the V4R, V5R, and V6R right-sided chest electrodes mirrors the placement of the V4, V5, and V6 left-sided chest electrodes. Specifically, when the ECG electrode patch 10 is accurately attached to the neonatal or infant patient's chest, the V4R electrode is placed approximately in the fifth right intercostal space at the right mid-clavicular line, the V5R electrode is placed approximately in the fifth right intercostal space at the same level as the V4R electrode at the right anterior axillary line, and the V6R electrode is placed approximately in the fifth right intercostal space at the same level as both the V4R and V5R electrodes at the right mid-axillary line.

Figure 3:
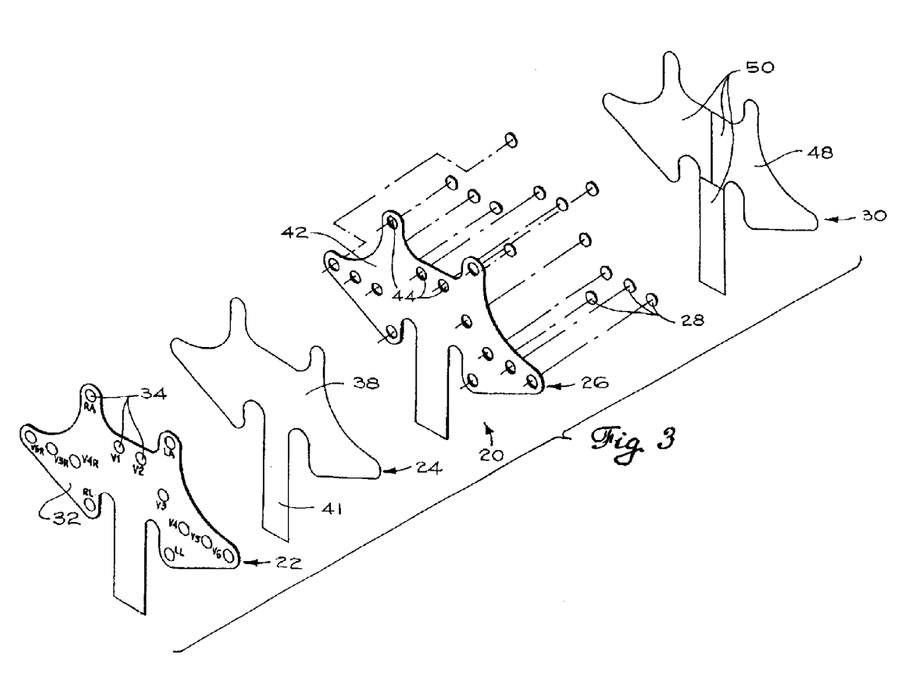
FIG. 3 is an exploded view of the front of the ECG electrode patch of FIG. 1.
Figure 4:
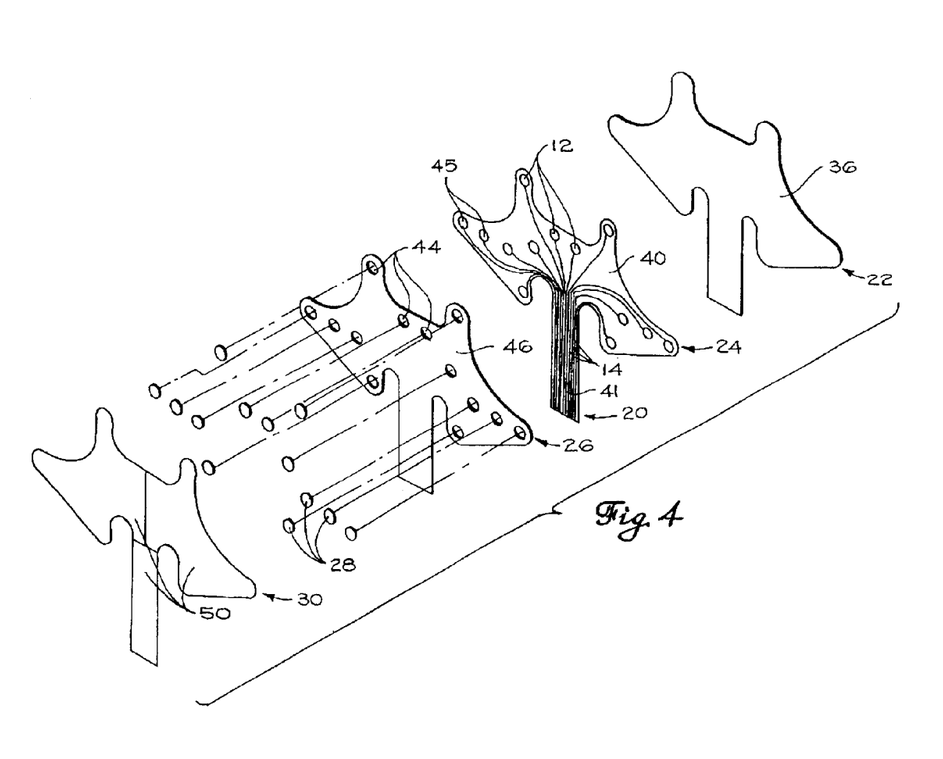
FIG. 4 is an exploded view of the back of the ECG electrode patch of FIG. 1.

As illustrated in FIGS. 3 and 4, the ECG electrode patch 10 includes a plurality of layers 20, including an outer flexible backing layer 22, a flexible substrate or flexible circuit board 24, an inner flexible backing layer 26, a plurality of conductive gel layers 28, and a multi-tab releasable liner layer 30.

Preferably, the outer flexible backing layer 22 is comprised of a non-conductive material, such as an insulating foam or a woven cloth material. As illustrated in FIG. 3, the outer flexible backing layer 22 includes an outer surface 32 that is the outer-most surface of the ECG electrode patch 10 and is positioned furthest from the patient's skin when the ECG electrode patch 10 is attached to the patient.

Preferably, the outer surface 32 of the outer flexible backing layer 22 is imprinted with a plurality of labels 34 indicating the location of the plurality of electrodes 12 within the ECG electrode patch 10. The purpose of the plurality of labels 34 is to assist the clinician in accurately attaching the ECG electrode patch 10 to the patient. The outer surface 32 of the outer flexible backing layer 22 may also include an additional label (not shown) indicating the proper placement of the ECG electrode patch 10 with respect to the patient's sternum.

As illustrated in FIG. 4, the outer flexible backing layer 22 includes an inner surface 36. Referring to FIGS. 3 and 4, the inner surface 36 of the outer flexible backing layer 22 is attached to an outer surface 38 of the substrate 24. The inner surface 36 of the outer flexible backing layer 22 is attached to the outer surface 38 of the substrate 24 with an adhesive (not shown), such as an acrylic adhesive.

The substrate 24 is preferably comprised of at least one layer of a flexible polymer material or a flexible polyester film. Most preferably, the substrate 24 is comprised of a 0.003 to 0.005 inch layer of polyester film. The substrate 24 may also include a plurality of substrate layers (not shown).

Referring to FIG. 4, the substrate 24 includes an inner surface 40. Overlaying the inner surface 40 of the substrate 24 is a plurality of electrodes 12 and a plurality of electrical conductors 14. Each one of the plurality of electrical conductors 14 is coupled to a one of the plurality of electrodes 12. The plurality of electrical conductors 14 extend from the plurality of electrodes 12 to an extension member 41 of the substrate 24. The plurality of electrical conductors 14 are aligned in a substantially parallel manner along the length of the extension member 41. If the substrate 24 includes a plurality of layers, the plurality of electrodes 12 and the plurality of electrical conductors 14 may be imbedded within the plurality of layers of the substrate 24 in order to conserve space on the inner surface 40 of the substrate 24.

Preferably, each one of the plurality of electrodes 12 is a silver/silver chloride electrode. Each one of the plurality of electrodes 12 may also be a carbon contact with a silver/silver chloride coating. Preferably, each one of the plurality of electrical conductors 14 is a carbon tracing.

As illustrated in FIG. 3, the inner flexible backing layer 26 includes an outer surface 42. Referring to FIGS. 3 and 4, the inner surface 40 of the substrate 24 is attached to the outer surface 42 of the inner flexible backing layer 26. The inner surface 40 of the substrate 24 is preferably attached to the outer surface 42 of the inner flexible backing layer 26 with an adhesive (not shown), such as an acrylic adhesive. The inner flexible backing layer 26 is preferably comprised of a non-conductive material, such as an insulating foam or a woven cloth material.

The inner flexible backing layer 26 includes a plurality of electrode windows 44. Each one of the plurality of electrode windows 44 corresponds to the location of a one of the plurality of electrodes 12. Preferably, the inner flexible backing layer 26 and the plurality of electrode windows 44 insulate the plurality of electrical conductors 14, but do not insulate the plurality of electrodes 12.

The plurality of conductive gel layers 28 are positioned within the plurality of electrode windows 44 and are coupled to skin-interface surfaces 45 of each of the plurality of electrodes 12 in order to enhance the conductive properties of the plurality of electrodes 12. Preferably, the conductive gel of the plurality of conductive gel layers 28 is a hydrogel electrolyte with adhesive characteristics. Specifically, the characteristics of the conductive gel preferably allow the conductive gel to bond to the electrodes, to bond to the patient's skin, and to provide an electrical conductor between the electrodes and the patient's skin. Most preferably, the conductive gel is suitable for attachment to a neonatal or infant patient's skin, which is more fragile and more sensitive than an adult patient's skin.

As illustrated in FIG. 4, the inner flexible backing layer 26 includes a skin-interface surface 46. When the ECG electrode patch 10 is fully assembled, the inner surface 46 of the inner flexible backing layer 26 is comprised of an insulating foam or a woven cloth material interspersed with a plurality of conductive gel layers 28. A skin adhesive (not shown) is coupled to the insulating foam or woven cloth material of the skin-interface surface 46. Preferably, the skin adhesive is biocompatible, non-conductive, pressure-sensitive, and has adhesive characteristics for attachment to and easy removal from a patient's skin. Most preferably, the skin adhesive is suitable for attachment to a neonatal or infant patient's skin, which is more fragile and more sensitive than an adult patient's skin.

In another preferred embodiment, rather than including both the plurality of conductive gel layers 28 and the non-conductive skin adhesive, a single conductive hydrogel with adhesive characteristics is coupled to the skin-interface surfaces 45 of each of the plurality of electrodes 12 and to the skin-interface surface 46 of the inner flexible backing layer 26.

Referring to FIGS. 3 and 4, in order to protect the adhesive and the plurality of conductive gel layers 28 from the environment before the ECG electrode patch 10 is used, an outer surface 48 of the multi-tab releasable liner 30 is attached to the skin-interface surface 46 of the inner flexible backing layer 26. The multi-tab releasable liner 30 is attached to the inner flexible backing layer 26 by virtue of the skin adhesive coupled to the skin-interface surface 46 and the adhesive characteristics of the plurality of conductive gel layers 28. Preferably, the releasable liner 30 is comprised of a plurality of tabs 50, rather than a single tab. The plurality of tabs 50 may be removed individually to allow certain portions of the ECG electrode patch 10 to be attached to the patient before other portions of the ECG electrode patch 10 are attached to the patient. The plurality of tabs 50 allow for easy positioning and attaching of the ECG electrode patch 10 to the patient by the clinician. The plurality of tabs 50 includes at least two tabs, but the plurality of tabs 50 may include any number of tabs in any type of configuration. Each one of the plurality of tabs 50 of the multi-tab releasable liner 30 is preferably comprised of a wax-covered paper material.

In the embodiment shown in the drawings and described, the ECG electrode patch 10 is a disposable medical device. However, in another preferred embodiment, the ECG electrode patch 10 is a reusable medical device. Referring to FIGS. 3 and 4, the reusable version of the ECG electrode patch 10 does not include the plurality of conductive gel layers 28, the skin adhesive layer (not shown), or the releasable liner layer 30. Rather, a conductive hydrogel with adhesive characteristics is manually applied by a clinician to the skin-interface surface 46 of the inner flexible backing layer 26. In the reusable version of the ECG electrode patch 10, the outer flexible backing layer 22, the substrate 24, and the inner flexible backing layer 26 are each constructed of thicker or otherwise more durable materials that are suitable for repeated uses.

Figure 5:
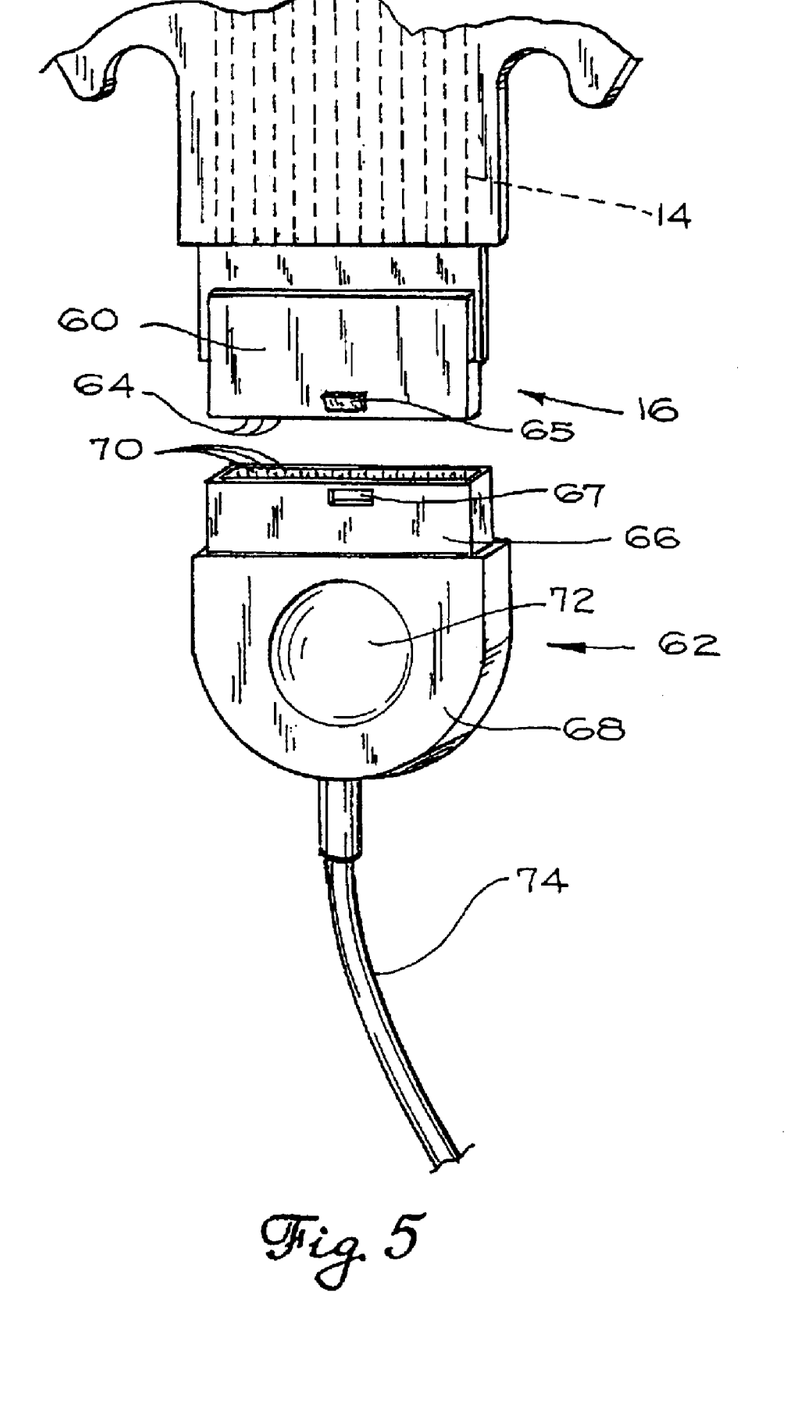
FIG. 5 is a perspective view of a connector for releasably coupling the ECG electrode patch of FIG. 1 to an ECG machine.

As illustrated in FIG. 5, the plurality of electrical conductors 14 are preferably coupled to the common connector 16. The common connector 16 includes a male connector 60 with a plurality of male connection terminals 64. The number of terminals in the plurality of male connection terminals 64 is equal to the number of conductors in the plurality of electrical conductors 14. The plurality of male connection terminals 64 includes thirteen terminals.

The common connector 16 is releasably coupleable to an adapter 62. The male connector 60 of the common connector 16 includes a flange 65 which forms a first part of an integral latch between the common connector 16 and the adapter 62.

The adapter 62 includes a female connector 66. Preferably, the female connector 66 includes a slot 67 which forms a second part of the integral latch between the common connector 16 and the adapter 62. The slot 67 of the female connector 66 is positioned to receive the flange 65 of the male connector 60. When the male connector 60 is slid into the female connector 66, the flange 65 of the male connector 60 slides within the female connector 66 until the flange 65 slides into the slot 67 of the female connector 66. When the flange 65 is positioned within the slot 67, the common connector 16 is prevented from accidentally separating from the adapter 62.

Although the integral latch is described as being comprised of a flange and a slot, the integral latch may be configured in any manner to prevent the common connector 16 from accidentally separating from the adapter 62.

The female connector 66 includes a plurality of female connection terminals 70 adapted to accept the plurality of male connection terminals 64 of the common connector 16. The number of terminals in the plurality of male connection terminals 64 is equal to the number of terminals in the plurality of female connection terminals 70. The plurality of female connection terminals 70 includes thirteen terminals.

The adapter 62 includes a body portion 68 coupled to the female connector 66. The body portion 68 is designed to be grasped by the clinician in order to releasably couple the female connector 66 of adapter 62 to the male connector 60 of the common connector 16. The top and bottom sides of the body portion 68 of the adapter 60 each include an indented portion 72 in which the clinician can place his thumb and forefinger, respectfully, in order to grasp the adapter 62.

Figure 6:
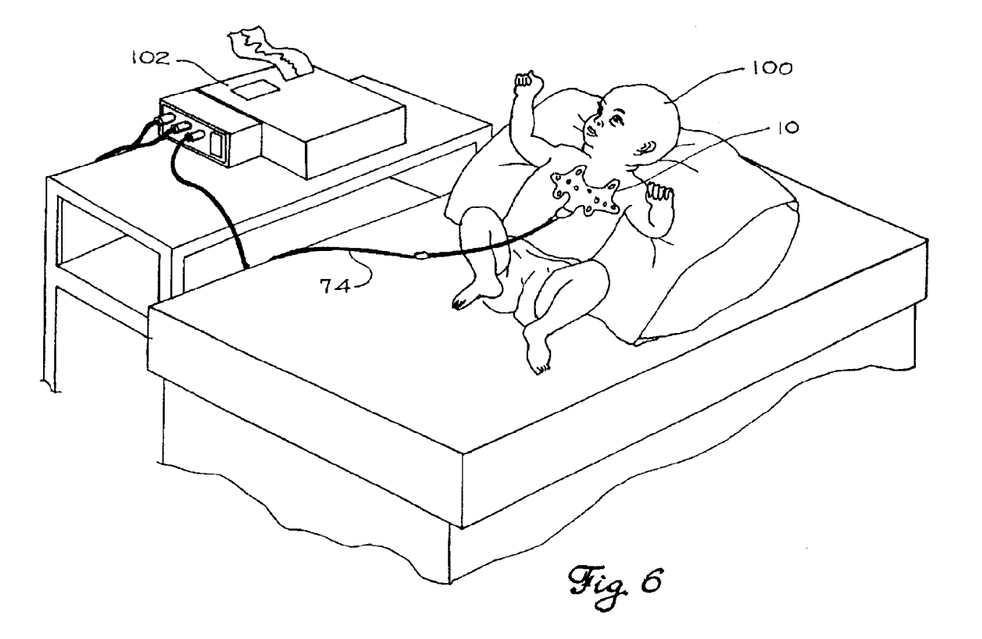
FIG. 6 illustrates the ECG electrode patch of FIG. 1 attached to an infant patient and coupled to an ECG machine.

Referring to FIGS. 5 and 6, the body portion 68 of the adapter 62 is also coupled to a single conductor cable 74, in lieu of up to thirteen conventional leadwires. The single conductor cable 74 is suitable for attachment to an ECG machine 102 (as shown in FIG. 6). The common connector 16, the adapter 62, and the single conductor cable 74 form a low-profile connection between the ECG electrode patch 10 and the ECG machine 102, i.e. the connection between the ECG electrode patch 10 and the ECG machine 102 is made close to the patient's body in a manner that reduces the accidental separation of the connection while the ECG data is being acquired.

Referring to FIGS. 4 and 5, although the connection between the ECG electrode patch 10 and the single conductor cable 74 is described as being comprised of the common conductor 16 and the adapter 62, the connection may be made in any manner. For example, in another preferred embodiment, the plurality of electrical conductors 14 is not coupled to the male connector 60. Rather, the plurality of electrical conductors 14 is formed into a straight or folded common connector without a connector housing. Rather than being located within a connector housing, the plurality of electrical conductors 14 form a straight common connector by simply extending straight from the extension member 41 (as shown in FIG. 4) of ECG electrode patch 10. Alternatively, the plurality of electrical conductors 14 form a folded common connector by extending from the extension member 41 and then folding over the extension member 41. The straight or folded common connector is coupleable to crimp-type terminal contacts located within a mating connector, in lieu of the female connector 66 of adapter 62, which is common in the printed circuit board industry. Straight or folded common connectors are typical of connector systems that have a pressure-type connector system or a low-insertion-force-type connector system. Folded common connectors are useful if the materials for the substrate 24 and flexible backing layers 22 and 26 are thin and require additional mechanical rigidity.

Referring to FIGS. 3–6, according to the method of the invention, the clinician first positions the ECG electrode patch 10 by referring to the plurality of labels 34 on the outer surface 32 of the outer flexible backing layer 22. If the clinician is trained in the positioning of ECG electrodes, the clinician can position the ECG electrode patch 10 according to the location of the electrodes designated by the plurality of labels 34. If the clinician is not trained in the positioning of ECG electrodes, the clinician can position the ECG electrode patch according to an additional label (not shown) on the outer surface 32 of the outer flexible backing layer 22 designating the proper placement of the ECG electrode patch 10 with respect to the patient's sternum.

After positioning the ECG electrode patch 10, the clinician selectively removes each one of the plurality of tabs 50 of the multi-tab releasable liner 30 from the ECG electrode patch 10 in order to expose the skin adhesive. As each one of the plurality of tabs 50 is removed from the multi-tab releasable liner 30, the clinician positions the portion of the ECG electrode patch 10 with the exposed skin adhesive near the chest of an infant patient 100 (as shown in FIG. 6). The clinician attaches each portion of the ECG electrode patch 10 with the exposed skin adhesive to the chest of the infant patient 100 by pressing firmly on the outer surface 32 of the outer flexible backing layer 22.

Either before or after attaching the ECG electrode patch 10 to the infant patient 100, the clinician couples the adapter 62 to the common connector 16 of the ECG electrode patch 10. The clinician slides the female connector 66 of the adapter 62 over the male connector 60 of the common connector 16 until the flange 65 is positioned within the slot 67. The clinician couples the single conductor cable 74 to the ECG machine 102. The clinician then acquires the ECG data for a multi-lead ECG from the infant patient 100.

Once the ECG data for the multi-lead ECG is acquired, the clinician detaches the single conductor cable 74 from the ECG electrode patch 10 by detaching the adapter 62 from the common connector 16. To detach the adapter 62 from the common connector 16, the clinician grasps the body portion 68 of the adapter 62 and pulls the adapter 62 away from the common connector 16 until the flange 65 releases from the slot 67.

Either before or after detaching the single conductor cable 74 from the ECG electrode patch 10, the clinician removes the ECG electrode patch 10 from the infant patient 100 by carefully pealing the ECG electrode patch 10 off of the chest of the infant patient 100. Finally, the clinician removes any conductive gel or skin adhesive remaining on the skin of the infant patient 100 in any conventional manner.

Various features and advantages of the invention are set forth in the following claims.

What is claimed is:

1. An ECG electrode patch suitable for attachment to a neonatal or infant patient's chest comprising:
   a substrate;
   a plurality of at least three electrodes coupled to the substrate, the plurality of electrodes including at least one electrode capable of measuring the electrical activity of the right side of the patient's heart, the plurality of electrodes acquiring data for generating a standard twelve-lead ECG and three additional leads of ECG data representing the electrical activity of the right side of the patient's heart; and
   a plurality of electrical conductors coupled to the plurality of electrodes and the substrate.

2. The ECG electrode patch of claim 1 wherein the at least one electrode capable of measuring the electrical activity of the right side of the patient's heart includes a one of (a) an electrode coupled to the substrate for attachment to the patient in approximately the fifth right intercostal space in the mid-clavicular line, (b) an electrode coupled to the substrate for attachment to the patient in approximately the fifth right intercostal space in the anterior axillary line, and (c) an electrode coupled to the substrate for attachment to the patient in approximately the fifth right intercostal space in the mid-axillary line.

3. The ECG electrode patch of claim 1 and further comprising a flexible backing layer coupled to the substrate.

4. The ECG electrode patch of claim 3 wherein the flexible backing layer is one of medical grade foam or woven cloth.

5. The ECG electrode patch of claim 3 wherein the flexible backing layer includes a skin-interface surface coupled to an adhesive.

6. The ECG electrode patch of claim 5 wherein each one of the plurality of electrodes includes a skin-interface surface coupled to a conductive gel.

7. The ECG electrode patch of claim 1 wherein the plurality of electrodes further includes up to six chest electrodes and up to four limb electrodes.

8. The ECG electrode patch of claim 1 wherein each one of the plurality of electrodes is a silver/silver chloride electrode.

9. The ECG electrode patch of claim 1 wherein the ECG electrode patch is labeled to identify the location of the electrodes.

10. The ECG electrode patch of claim 1 wherein the ECG electrode patch is labeled to identify proper placement of the patch with respect to the patient's sternum.

11. The ECG electrode patch of claim 1 wherein the plurality of electrical conductors are releasably connectable to an ECG machine with a single conductor.

12. The ECG electrode patch of claim 11 wherein the plurality of electrical conductors are releasably coupled to the single conductor with a connector, the connector including an integral latch.

13. The ECG electrode patch of claim 1 wherein the ECG electrode patch is a size suitable for attachment to a neonatal patient weighing less than approximately three kilograms.

14. The ECG electrode patch of claim 1 wherein the ECG electrode patch is a size suitable for attachment to an infant patient weighing up to approximately twenty kilograms.

15. The ECG electrode patch of claim 1 wherein the at least one electrode capable of measuring the electrical activity of the right side of the patient's heart is at least one electrode for attachment to the patient to the right of a patient's sagittal plane.

16. An ECG electrode patch suitable for attachment to a neonatal or infant patient's chest comprising:
   a substrate;
   a flexible backing layer coupled to the substrate, the flexible backing layer including a skin-interface surface coupled to an adhesive;
   a plurality of at least three electrodes coupled to the substrate, the plurality of electrodes including at least one electrode capable of measuring the electrical activity of the right side of the patient's heart, each one of the plurality of electrodes including a skin-interface surface coupled to a conductive gel, the plurality of electrodes acquiring data for generating a standard twelve-lead ECG and three additional leads of ECG data representing the electrical activity of the right side of the patient's heart;
   a plurality of electrical conductors coupled to the plurality of electrodes and to the substrate; and
   a releasable liner coupled to the adhesive and the conductive gel.

17. The ECG electrode patch of claim 16 wherein the releasable liner is a multi-tab releasable liner.

18. The ECG electrode patch of claim 16 wherein the at least one electrode capable of measuring the electrical activity of the right side of the patient's heart includes a one of (a) an electrode coupled to the substrate for attachment to the patient in approximately the fifth right intercostal space in the mid-clavicular line, (b) an electrode coupled to the substrate for attachment to the patient in approximately the fifth right intercostal space in the anterior axillary line, and (c) an electrode coupled to the substrate for attachment to the patient in approximately the fifth right intercostal space in the mid-axillary line.

19. The ECG electrode patch of claim 16 wherein the plurality of electrodes further includes up to six chest electrodes and up to four limb electrodes.

20. The ECG electrode patch of claim 16 wherein the flexible backing layer is one of medical grade foam or woven cloth.

21. The ECG electrode patch of claim 16 wherein each one of the plurality of electrodes is a silver/silver chloride electrode.

22. The ECG electrode patch of claim 16 wherein the ECG electrode patch is labeled to identify the location of the electrodes.

23. The ECG electrode patch of claim 16 wherein the ECG electrode patch is labeled to identify proper placement of the patch with respect to the patient's sternum.

24. The ECG electrode patch of claim 16 wherein the plurality of electrical conductors are releasably connectable to an ECG machine with a single conductor.

25. The ECG electrode patch of claim 24 wherein the plurality of electrical conductors are releasably coupled to the single conductor with a connector, the connector including an integral latch.

26. The ECG electrode patch of claim 16 wherein the ECG electrode patch is a size suitable for attachment to a neonatal patient weighing less than approximately three kilograms.

27. The ECG electrode patch of claim 16 wherein the ECG electrode patch is a size suitable for attachment to an infant patient weighing up to approximately twenty kilograms.

28. The ECG electrode patch of claim 16 wherein the at least one electrode capable of measuring the electrical activity of the right side of the patient's heart is at least one electrode for attachment to the patient to the right of a patient's sagittal plane.

29. A method of acquiring a neonatal or infant patient's ECG, the method comprising the acts of:
providing an ECG electrode patch including a plurality of at least three electrodes, the plurality of electrodes including at least one electrode capable of measuring the electrical activity of the right side of the patient's heart;
attaching the ECG electrode patch to the patient's chest;
acquiring data for an ECG from the plurality of electrodes; and
generating a standard twelve-lead ECG with three additional leads of ECG data representing the electrical activity of the right side of the patient's heart from the acquired data.

30. The method of claim 29 wherein the act of providing a plurality of electrodes including at least one electrode capable of measuring the electrical activity of the right side of the patient's heart includes providing a one of (a) an electrode for attachment to the patient in approximately the fifth right intercostal space in the mid-clavicular line, (b) an electrode for attachment to the patient in approximately the fifth right intercostal space in the anterior axillary line, and (c) an electrode for attachment to the patient in approximately the fifth right intercostal space in the mid-axillary line.

31. The method of claim 29 wherein the act of providing a plurality of electrodes further includes providing up to six chest electrodes and up to four limb electrodes.

32. The method of claim 29 wherein the act of attaching the ECG electrode patch to the patient's chest includes attaching the ECG electrode patch according to the location of the electrodes as labeled on the ECG electrode patch.

33. The method of claim 29 wherein the act of attaching the ECG electrode patch to the patient's chest includes attaching the ECG electrode patch according to a label on the ECG electrode patch designating the proper placement of the ECG electrode patch with respect to the patient's sternum.

34. The method of claim 29 and further comprising the act of detaching a releasable liner from the ECG electrode patch before the act of attaching the ECG electrode patch to the patient's chest.

35. The method of claim 29 and further comprising the act of releasably coupling the ECG electrode patch to an ECG machine with a single conductor.

36. The method of claim 29 wherein the act of attaching the ECG electrode patch to the patient's chest includes attaching the ECG electrode patch so that the at least one electrode capable of measuring the electrical activity of the right side of the patient's heart is attached to the right of a patient's sagittal plane.

37. An ECG electrode patch suitable for attachment to a neonatal or infant patient's chest comprising:
a flexible circuit board including a plurality of electrical conductors coupled to a non-conductive material;
a plurality of at least three electrodes coupled to the non-conductive material and to the plurality of electrical conductors, the plurality of electrodes including at least one electrode capable of measuring the electrical activity of the right side of the patient's heart, the plurality of electrodes acquiring data for generating a standard twelve-lead ECG and three additional leads of ECG data representing the electrical activity of the right side of the patient's heart;
an adhesive coupled to a skin-interface surface of the non-conductive material;
a conductive gel coupled to a skin-interface surface of each one of the plurality of electrodes; and
a releasable liner coupled to the adhesive and the conductive gel.

38. The ECG electrode patch of claim 37 wherein the at least one electrode capable of measuring the electrical activity of the right side of the patient's heart includes a one of (a) an electrode for attachment to the patient in approximately the fifth right intercostal space in the mid-clavicular line, (b) an electrode for attachment to the patient in approximately the fifth right intercostal space in the anterior axillary line, and (c) an electrode for attachment to the patient in approximately the fifth right intercostal space in the mid-axillary line.

39. The ECG electrode patch of claim 37 and further comprising a flexible backing layer coupled to the flexible circuit board.

40. The ECG electrode patch of claim 39 wherein the flexible backing layer is one of medical grade foam or woven cloth.

41. The ECG electrode patch of claim 37 wherein the releasable liner is a multi-tab releasable liner.

42. The ECG electrode patch of claim 37 wherein the plurality of electrodes further includes up to six chest electrodes and up to four limb electrodes.

43. The ECG electrode patch of claim 37 wherein each one of the plurality of electrodes is a silver/silver chloride electrode.

44. The ECG electrode patch of claim 37 wherein the ECG electrode patch is labeled to identify the location of the electrodes.

45. The ECG electrode patch of claim 37 wherein the ECG electrode patch is labeled to identify proper placement of the patch with respect to the patient's sternum.

46. The ECG electrode patch of claim 37 wherein the plurality of electrical conductors are releasably connectable to an ECG machine with a single conductor.

47. The ECG electrode patch of claim 46 wherein the plurality of electrical conductors are releasably coupled to the single conductor with a connector, the connector including an integral latch.

48. The ECG electrode patch of claim 37 wherein the ECG electrode patch is a size suitable for attachment to a neonatal patient weighing less than approximately three kilograms.

49. The ECG electrode patch of claim 37 wherein the ECG electrode patch is a size suitable for attachment to an infant patient weighing up to approximately twenty kilograms.

50. The ECG electrode patch of claim 37 wherein the at least one electrode capable of measuring the electrical activity of the right side of the patient's heart is at least one electrode for attachment to the patient to the right of a patient's sagittal plane.

51. An ECG electrode patch suitable for attachment to a neonatal or infant patient's chest comprising:
    a substrate;
    a plurality of at least three electrodes coupled to the substrate, the plurality of electrodes including up to six electrodes capable of measuring the electrical activity of the left side of the patient's heart, up to four limb electrodes, and up to three electrodes capable of measuring the electrical activity of the right side of the patient's heart, the plurality of electrodes acquiring data for generating a standard twelve-lead ECG and three additional leads of ECG data representing the electrical activity of the right side of the patient's heart; and
    a plurality of electrical conductors coupled to the plurality of electrodes and the substrate.

52. The ECG electrode patch of claim 51 wherein the up to three electrodes capable of measuring the electrical activity of the right side of the patient's heart includes a one of (a) an electrode coupled to the substrate for attachment to the patient in approximately the fifth right intercostal space in the mid-clavicular line, (b) an electrode coupled to the substrate for attachment to the patient in approximately the fifth right intercostal space in the anterior axillary line, and (c) an electrode coupled to the substrate for attachment to the patient in approximately the fifth right intercostal space in the mid-axillary line.

53. The ECG electrode patch of claim 51 and further comprising a flexible backing layer coupled to the substrate.

54. The ECG electrode patch of claim 53 wherein the flexible backing layer is one of medical grade foam or woven cloth.

55. The ECG electrode patch of claim 53 wherein the flexible backing layer includes a skin-interface surface coupled to an adhesive.

56. The ECG electrode patch of claim 55 wherein each one of the plurality of electrodes includes a skin-interface surface coupled to a conductive gel.

57. The ECC electrode patch of claim 56 and further comprising a releasable liner coupled to the adhesive and the conductive gel.

58. The ECG electrode patch of claim 57 wherein the releasable liner is a multi-tab releasable liner.

59. The ECG electrode patch of claim 51 wherein each one of the plurality of electrodes is a silver/silver chloride electrode.

60. The ECG electrode patch of claim 51 wherein the ECG electrode patch is labeled to identify the location of the electrodes.

61. The ECG electrode patch of claim 51 wherein the ECG electrode patch is labeled to identify proper placement of the patch with respect to the patient's sternum.

62. The ECG electrode patch of claim 51 wherein the plurality of electrical conductors are releasably connectable to an ECG machine with a single conductor.

63. The ECG electrode patch of claim 62 wherein the plurality of electrical conductors are releasably coupled to the single conductor with a connector, the connector including an integral latch.

64. The ECG electrode patch of claim 51 wherein the ECG electrode patch is a size suitable for attachment to a neonatal patient weighing less than approximately three kilograms.

65. The ECG electrode patch of claim 51 wherein the ECG electrode patch is a size suitable for attachment to an infant patient weighing up to approximately twenty kilograms.

66. The ECG electrode patch of claim 51 wherein:
    the up to six electrodes capable of measuring the electrical activity of the left side of the patient's heart is at least one electrode for attachment to the patient to the left of a patient's sagittal plane; and
    the up to three electrodes capable of measuring the electrical activity of the right side of the patient's heart is at least one electrode for attachment to the patient to the right of the patient's sagittal plane.

67. An ECG electrode patch suitable for attachment to a neonatal or infant patient's chest comprising:
    a substrate;
    a plurality of at least three electrodes coupled to the substrate in a plurality of fixed positions, the plurality of electrodes including
        at least one electrode capable of measuring the electrical activity from the left side of the patient's heart;
        at least one limb electrode; and
        at least one electrode capable of measuring the electrical activity from the right side of the patient's heart; and
    a plurality of electrical conductors coupled to the plurality of electrodes and the substrate.

68. The ECG electrode patch of claim wherein:
    the at least one electrode capable of measuring the electrical activity from the left side of the patient's heart is at least one electrode for attachment to the patient to the left of a patient's sagittal plane; and
    the at least one electrode capable of measuring the electrical activity from the right side of the patient's heart is at least one electrode for attachment to the patient to the right of the patient's sagittal plane.

69. The ECG electrode patch of claim 67 wherein the at least one electrode capable of measuring the electrical activity of the right side of the patient's heart includes at least one of (a) an electrode for attachment to the patient in approximately the fifth right intercostal space in the mid-clavicular line, (b) an electrode for attachment to the patient in approximately the fifth right intercostal space in the anterior axillary line, and (c) an electrode for attachment to the patient in approximately the fifth right intercostal space in the mid-axillary line.

70. The ECG electrode patch of claim 67 and further comprising a flexible backing layer coupled to the substrate.

71. The ECG electrode patch of claim 70 wherein the flexible backing layer is one of medical grade foam or woven cloth.

72. The ECG electrode patch of claim 70 wherein the flexible backing layer includes a skin-interface surface coupled to an adhesive.

73. The ECG electrode patch of claim 72 wherein each one of the plurality of electrode includes a skin-interface surface coupled to a conductive gel.

74. The ECG electrode patch of claim 73 and further comprising a releasable liner coupled to the adhesive and the conductive gel.

75. The ECG electrode patch of claim 74 wherein the releasable liner is a multi-tab releasable liner.

76. The ECG electrode patch of claim 67 wherein the plurality of electrodes includes six electrodes capable of measuring the electrical activity from the left side of the patient's heart, four limb electrodes, and three electrodes capable of measuring the electrical activity from the right side of the patient's heart.

77. The ECG electrode patch of claim 67 wherein the plurality of electrodes acquire data for generating a standard twelve-lead ECG and three additional leads of ECG data representing the electrical activity of the patient's heart from the right side of the heart.

78. The ECG electrode patch of claim 67 wherein each one of the plurality of electrodes is a silver/silver chloride electrode.

79. The ECG electrode patch of claim 67 wherein the ECG electrode patch is labeled to identify the location of the electrodes.

80. The ECG electrode patch of claim 67 wherein the ECG electrode patch is labeled to identify proper placement of the patch with respect to the patient's sternum.

81. The ECG electrode patch of claim 67 wherein the plurality of electrical conductors are releasably connectable to an ECG machine with a single conductor.

82. The ECG electrode patch of claim 81 wherein the plurality of electrical conductors are releasably coupled to the single conductor with a connector, the connector including an integral latch.

83. The ECG electrode patch of claim 67 wherein the ECG electrode patch is a size suitable for attachment to a neonatal patient weighing less than approximately three kilograms.

84. The ECG electrode patch of claim 67 wherein the ECG electrode patch is a size suitable for attachment to an infant patient weighing up to approximately twenty kilograms.

85. An ECG electrode patch suitable for attachment to a neonatal or infant patient's chest comprising:

a substrate; and means rigidly connected to the substrate in fixed positions for simultaneously measuring the electrical activity of the patient's heart from the left side of the heart, the electrical activity of the patient's heart from the perspective of a limb electrode, and the electrical activity of the patient's heart from the right side of the heart.

86. The ECG electrode patch of claim 85 wherein:

the means for measuring the electrical activity of the patient's heart from the left side of the heart is at least one electrode for attachment to the patient to the left of a patient's sagittal plane; and the means for measuring the electrical activity of the patient's heart from the right side of the heart is at least one electrode for attachment to the patient to the right of the patient's sagittal plane.

87. The ECG electrode patch of claim 85 wherein the means for measuring the electrical activity of the patient's heart from the right side of the heart includes at least one of (a) an electrode for attachment to the patient in approximately the fifth right intercostal space in the mid-clavicular line, (b) an electrode for attachment to the patient in approximately the fifth right intercostal space in the anterior axillary line, and (c) an electrode for attachment to the patient in approximately the fifth right intercostal space in the mid-axillary line.

88. The ECG electrode patch of claim 85 wherein the means for measuring the electrical activity of the patient's heart is a plurality of electrodes including six electrodes capable of measuring the electrical activity from the left side of the heart, four limb electrodes, and three electrodes capable of measuring the electrical activity from the right side of the heart.

89. The ECG electrode patch of claim 85 wherein the means for measuring the electrical activity of the patient's heart is capable of acquiring data for generating a standard twelve-lead ECG and three additional leads of ECG data representing the electrical activity of the patient's heart from the right side of the heart.

* * * * *

UNITED STATES PATENT AND TRADEMARK OFFICE
CERTIFICATE OF CORRECTION

PATENT NO.    : 6,453,186 B1                                               Page 1 of 1
DATED         : September 17, 2002
INVENTOR(S)   : David Anthony Lovejoy et al.

It is certified that error appears in the above-identified patent and that said Letters Patent is hereby corrected as shown below:

<u>Column 14,</u>
Line 38, insert -- 67 -- after the word "claim"

Signed and Sealed this

Eleventh Day of February, 2003

JAMES E. ROGAN
*Director of the United States Patent and Trademark Office*